United States Patent
Chen et al.

(10) Patent No.: US 10,408,966 B2
(45) Date of Patent: Sep. 10, 2019

(54) INSPECTION DEVICES, INSPECTION METHODS AND INSPECTION SYSTEMS

(71) Applicants: Tsinghua University, Beijing (CN); Nuctech Company Limited, Beijing (CN)

(72) Inventors: Zhiqiang Chen, Beijing (CN); Li Zhang, Beijing (CN); Tianyi Yangdai, Beijing (CN); Qingping Huang, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 346 days.

(21) Appl. No.: 15/122,659

(22) PCT Filed: Mar. 3, 2015

(86) PCT No.: PCT/CN2015/073558
§ 371 (c)(1),
(2) Date: Aug. 31, 2016

(87) PCT Pub. No.: WO2015/131802
PCT Pub. Date: Sep. 11, 2015

(65) Prior Publication Data
US 2017/0075026 A1    Mar. 16, 2017

(30) Foreign Application Priority Data
Mar. 4, 2014    (CN) .......................... 2014 1 0075765

(51) Int. Cl.
*G01T 1/00*    (2006.01)
*G01V 5/00*    (2006.01)
(Continued)

(52) U.S. Cl.
CPC ......... *G01V 5/0025* (2013.01); *G01N 23/083* (2013.01); *G01N 23/10* (2013.01);
(Continued)

(58) Field of Classification Search
CPC .. G01N 2223/643; G01T 1/36; G01V 5/0025; G01V 5/0066
See application file for complete search history.

(56) References Cited

U.S. PATENT DOCUMENTS

| | | | |
|---|---|---|---|
| 7,116,751 B2 | 10/2006 | Ellenbogen et al. | |
| 2003/0031295 A1* | 2/2003 | Harding | G01N 23/201 378/86 |

(Continued)

FOREIGN PATENT DOCUMENTS

| | | |
|---|---|---|
| CN | 1146890 A | 4/1997 |
| CN | 103153190 A | 6/2013 |

(Continued)

OTHER PUBLICATIONS

Second Office Action for Chinese Patent Application No. 201410075765.1, dated Feb. 7, 2018, 7 pages.

(Continued)

*Primary Examiner* — Dani Fox
(74) *Attorney, Agent, or Firm* — Westman, Champlin & Koehler, P.A.

(57) ABSTRACT

The present disclosure discloses an inspection device, an inspection method and an inspection system. The device comprises a distributed ray source comprising multiple source points; a light source collimator configured to converge the rays generated by the distributed ray source to form an inverted fan-shaped ray beam; a scatter collimator configured to only allow rays scattered at one or more particular scattering angles which are generated by the rays from the light source collimator interacting with inspected (Continued)

objects to pass; at least one detector each comprising multiple detection units which have an energy resolution capability and are substantially arranged in a cylindrical surface to receive the scattered rays passing through the scatter collimator; and a processing apparatus configured to calculate energy spectrum information of the scattered rays from the inspected objects based on a signal output by the detectors.

14 Claims, 10 Drawing Sheets

(51) Int. Cl.
  *G01N 23/10* (2018.01)
  *G01N 23/083* (2018.01)
  *G01T 1/36* (2006.01)
(52) U.S. Cl.
  CPC .............. *G01T 1/36* (2013.01); *G01V 5/0033* (2013.01); *G01V 5/0066* (2013.01); *G01N 2223/50* (2013.01); *G01N 2223/643* (2013.01)

(56) References Cited

U.S. PATENT DOCUMENTS

| | | | |
|---|---|---|---|
| 2008/0285706 A1* | 11/2008 | Schlomka | A61B 6/032 378/6 |
| 2010/0061512 A1* | 3/2010 | Edic | G01N 23/20 378/71 |
| 2013/0204113 A1 | 8/2013 | Carmi | |

FOREIGN PATENT DOCUMENTS

| | | |
|---|---|---|
| CN | 103330570 A | 10/2013 |
| CN | 103385732 A | 11/2013 |
| JP | 2000235007 A | 8/2000 |
| WO | 2004090576 A2 | 10/2004 |
| WO | 2012049590 A1 | 4/2012 |

OTHER PUBLICATIONS

International Search Report and Written Opinion for International Application No. PCT/CN2015/073558, dated May 28, 2015, 7 pages.
First Office Action from Chinese Patent Application No. 201410075765.1, dated Mar. 29, 2017, 15 pages.
First Examination Report from Australian Patent Application No. 2015226613, dated Nov. 22, 2016, 3 pages.
Second Examination Report from Australian Patent Application No. 2015226613, dated Nov. 13, 2017, 4 pages.
Notification of Reason for Refusal from Korean Patent Application No. 10-2016-7026749, dated Jun. 16, 2017 pages.
Notice of Final Rejection from Korean Patent Application No. 10-2016-7026749, dated Dec. 19, 2017, 5 pages.
Communication from European Patent Application No. 15759349.2, dated Sep. 15, 2017, 8 pages.
Notification of Reasons for Refusal from Japanese Patent Application No. 2016-558258, dated Jun. 2, 2017, 6 pages.

* cited by examiner

INSPECTION DEVICES, INSPECTION METHODS AND INSPECTION SYSTEMS

CROSS-REFERENCE TO RELATED APPLICATION

This Application is a Section 371 National Stage Application of International Application No. PCT/CN2015/073558, filed 03 Mar. 2015 and published as WO 2015/131802 A1 on 11 Sep. 2015, in Chinese, the contents of which are hereby incorporated by reference in their entirety.

TECHNICAL FIELD

The present disclosure relates to inspection systems based on a coherent X-ray scattering technology, and in particular, to inspection devices, inspection methods, and inspection systems for determining whether inspected object includes particular content such as explosives, dangerous articles or the like.

BACKGROUND

More and more attention is paid to detection of explosives, drugs or the like in objects such as luggage. Some detection measures, for example, Computer Tomography (CT) detection technology, may obtain important information such as a spatial position distribution, density, mass, an effective atomic number or the like of various materials in the luggage, so as to recognize categories of different materials. When a suspicious material is detected by a system, an alarm is generated and the suspicious material is delivered to a detection apparatus in next stage for detection or the suspicious material is detected manually.

However, it is still of a high error rate to judge whether a certain material is an explosive by using information such as density, an atomic number or the like. In order to reduce the error rate of the whole system, reduce a number of manual detection operations and improve reliability of the system, a detection system based on coherent X-ray scattering is connected in series a CT detection system, which may significantly reduce the error rate of the system.

The coherent X-ray scattering (X-ray diffraction) technology is used to detect materials (which mostly are crystal materials), and is primarily based on the Bragg diffraction equation as follows:

$$n\lambda = 2d \sin(\theta/2) = \frac{nhc}{E} \quad (1)$$

wherein n is a diffraction emphasis level, and generally satisfies n=1 in explosive detection; $\lambda$ is a wavelength of an incident ray; d is a lattice spacing, and is also a lattice constant; $\theta$ is a deflection angle after rays are scattered; h is a Planck constant; c is a velocity of light; and E is energy of incident photons. When various parameters satisfy the above equation, coherence emphasis occurs, the corresponding scattering is elastic scattering, and the energy of the X photons is unchanged.

In a diffraction pattern based on an energy distribution, an angle $\theta$ at which the measurement is implemented by the detector is fixed, i.e., the energy spectrum of the scattered X-rays is measured at a fixed scattering angle. The lattice constant d and the energy E of the incident photons which satisfy the above equation are in a one-to-one relationship.

Thus, fingerprint features of the crystal materials, i.e., lattice constants $d_1, d_2, \ldots d_n$ may be determined according to the peak positions of the energy spectrums $E_1, E_2, \ldots E_n$, so that different materials may be recognized. For example, typical explosives primarily include different crystal materials, and the crystal types are recognized according to the lattice constants. Therefore, this method is an effective explosive detection measure.

A single-energy X-ray source may also be used to count X photons at different scattering angles. The crystal information is obtained according to a one-to-one relationship between $\theta$ and d. This method may reduce the requirements for the detector, but has higher requirements for monochromaticity of the light source. In addition, it is inefficient to change an angle for measurement. This method is applied in an experiential device, but is infrequently used in practical designs and applications.

A detection method based on an inverted fan-shaped beam is proposed. A system using an inverted fan-shaped beam achieves measurement in a fixed manner by using a few detectors. In the inverted fan-shaped structure, scattered rays from objects in different positions in a detection plane which are perpendicular to a direction of a beam of rays are converged to a point on the detectors, which results in superposition of spectral lines of objects in two positions. In order to obtain information of various pixels in a section plane of materials, multiple light source points cannot illuminate at the same time, and need to emit rays in a certain order. This results in significant degradation of intensity of rays in the detection plane at any time and a relatively low signal-to-noise ratio of data measured by the system in a case that the materials pass through the detection plane at a certain speed.

SUMMARY

In consideration of one or more problems in the related art, an inspection device, inspection method, and inspection system based on the coherent ray scattering technology are proposed, which have a three-dimensional positioning capability and a high resolution capability, achieves a high signal-to-noise ratio, and reduces the system cost.

According to an aspect of the present disclosure, an inspection device is provided, including: a distributed ray source comprising multiple source points to generate rays; a light source collimator arranged at a ray beam output end of the distributed ray source, and configured to converge the rays generated by the distributed ray source along fan-shaped radial lines to form an inverted fan-shaped ray beam; a scatter collimator configured to only allow rays scattered at one or more particular scattering angles which are generated by the rays from the light source collimator interacting with inspected objects to pass; at least one detector arranged on the downstream of the scatter collimator, each detector comprising multiple detection units which have an energy resolution capability and are substantially arranged in a cylindrical surface to receive the scattered rays passing through the scatter collimator; and a processing apparatus configured to calculate energy spectrum information of the scattered rays from the inspected objects based on a signal output by the detectors.

Preferably, the processing apparatus is further configured to calculate a lattice constant based on peak position information included in the energy spectrum information of the scattered rays, and judge whether the inspected objects include explosives or dangerous objects by comparing the calculated lattice constant with a predetermined value.

Preferably, the inspection device further comprises a control apparatus configured to control a particular source point in the distributed ray source to generate a ray according to input position information of an region of interest in the inspected objects to inspect the region of interest.

Preferably, the multiple source points of the distributed light source are distributed in an arc shape, a straight line shape, a U shape, an inverted U shape, an L shape, or an inverted L shape.

Preferably, the scatter collimator comprises a bottom surface and multiple embedded cylindrical surfaces on the bottom surface, circular slots are arranged at predetermined range intervals in the multiple embedded cylindrical surfaces, and a slot is arranged on the bottom surface along an axial direction of the cylindrical surfaces.

Preferably, the scatter collimator comprises a bottom surface and multiple embedded spherical surfaces on the bottom surface, circular slots are arranged at predetermined range intervals in the multiple embedded spherical surfaces, and a slot is arranged on the bottom surface along a radial direction of the bottom surface.

Preferably, the scatter collimator is made of a ray absorbing material.

Preferably, the scatter collimator comprises multiple columns of parallel coaxial conical surfaces made of a ray absorbing material.

Preferably, the scatter collimator comprises multiple parallel slices.

Preferably, the detector is a CdZnTe (CZT) detector or a High-Purity Ge (HPGe) detector.

According to another aspect of the present disclosure, an inspection system is provided, comprising: a bearing member configured to bear inspected objects to move linearly; a first scanning stage comprising a transmission imaging apparatus or a Computer Tomography (CT) imaging apparatus to implement transmission inspection or CT inspection on the inspected objects; a processing apparatus configured to receive a signal generated by the first scanning stage and determine at least one region of interest in the inspected objects based on the signal; a second scanning stage arranged a predetermined distance from the first scanning stage along a movement direction of the objects, the second scanning stage comprising: a distributed ray source comprising multiple source points to generate rays; a light source collimator arranged at a ray beam output end of the distributed ray source, and configured to converge the rays generated by the distributed ray source along fan-shaped radial lines to form an inverted fan-shaped ray beam; a scatter collimator configured to only allow rays scattered at one or more particular scattering angles which are generated by the rays from the light source collimator interacting with the inspected objects to pass; and detectors arranged on the downstream of the scatter collimator, each detector comprising multiple detection units which have an energy resolution capability and are substantially arranged in a cylindrical surface to receive the scattered rays passing through the scatter collimator; wherein the processing apparatus is configured to instruct the second scanning stage to inspect the at least one region of interest and calculate energy spectrum information of the scattered rays from the inspected objects based on the signal output by the detectors.

According to a further aspect of the present disclosure, an inspection method is provided, comprising: generating, by a distributed ray source comprising multiple source points, rays; converging the rays generated by the distributed ray source along fan-shaped radial lines to form an inverted fan-shaped ray beam; collimating, by a scatter collimator arranged on a front end of detectors, the rays to only allow rays scattered at one or more particular scattering angles which are generated by the rays interacting with inspected objects to pass; receiving, by detectors, the scattered rays passing through the scatter collimator, each detector having an energy resolution capability and is in a cylindrical surface shape; and calculating energy spectrum information of the scattered rays from the inspected objects based on a signal output by the detectors.

Preferably, the method further comprises steps of: calculating a lattice constant based on peak position information included in the energy spectrum information of the scattered rays, and judging whether the inspected objects include explosives or dangerous objects by comparing the calculated lattice constant with a predetermined value.

Preferably, the method further comprises steps of: controlling a particular source point in the distributed ray source to generate a ray according to input position information of a region of interest in the inspected objects to inspect the region of interest.

With the above technical solutions, corresponding parts of objects are illuminated by controlling several particular light source points in a distributed light source to emit rays, so as to implement targeted detection. In addition, due to the use of a cylindrical detector, signals of detection units in some positions may be obtained, and therefore a three-dimensional positioning capability is optimized, and intensity of signals is significantly enhanced.

BRIEF DESCRIPTION OF THE DRAWINGS

The following accompanying drawings facilitate better understanding the description of different embodiments of the present disclosure below. These accompanying drawings are not necessarily drawn to scale, and schematically illustrate primary features of some embodiments of the present disclosure. These accompanying drawings and implementations provide some embodiments of the present disclosure in a non-limiting and non-exhaustive manner. For conciseness, the same reference signs are used for the same or similar components or structures having the same functions in different accompanying drawings.

DETAILED DESCRIPTION

Some embodiments of the present disclosure will be described in detail below. In the following description, some specific details, for example, specific structures and specific parameters of components in the embodiments, are used to provide better understanding of the embodiments of the present disclosure. Those skilled in the art may understand that even if some details are omitted or other methods, elements, materials or the like are incorporated, the embodiments of the present disclosure may also be implemented.

Figure 1:
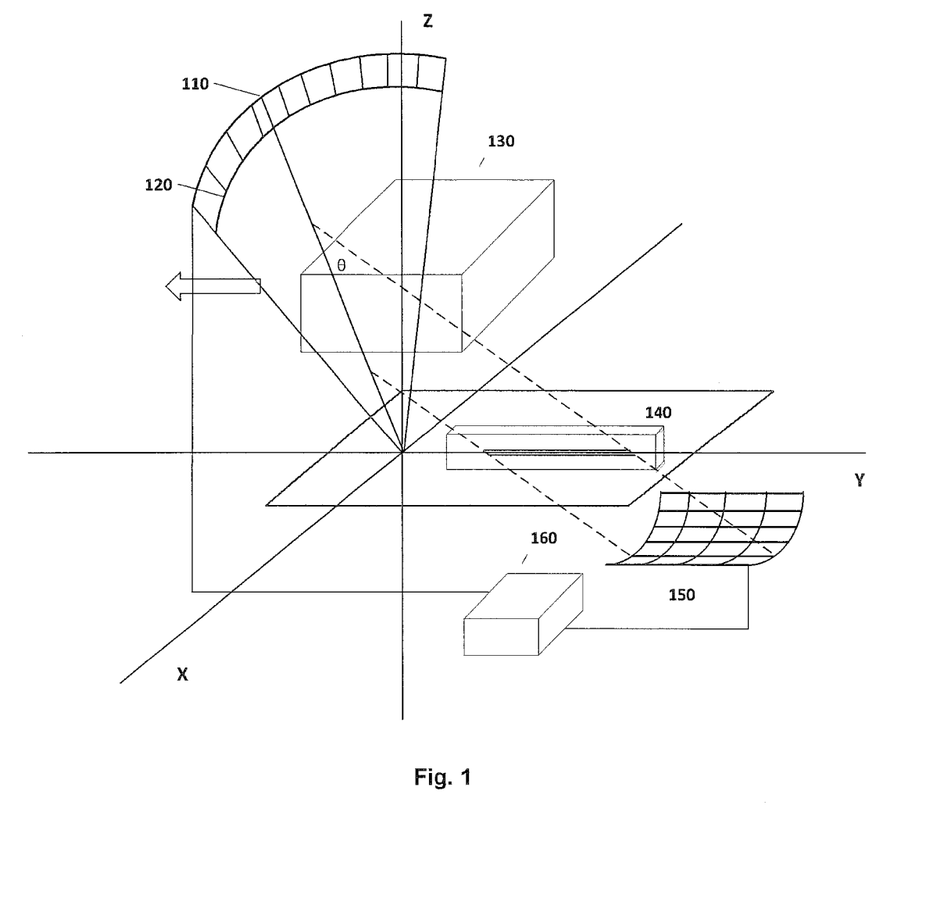
FIG. 1 is a structural diagram of an inspection device according to an embodiment of the present disclosure.

FIG. 1 illustrates a structural diagram of an inspection device according to an embodiment of the present disclosure. As shown in FIG. 1, the illustrated inspection device inspects inspected objects 130, and includes a distributed light source 110, a light source collimator 120 in front of the distributed light source 110, a scatter collimator 140, and a detector 150. As shown, the light source collimator 120 converges X-rays to an origin of a coordinate system along a radial direction of a fan-shaped beam. The scatter collimator 140 is arranged above an XOY plane. The detector is cylindrical detector with an axis of Y axis, and includes multiple detection units arranged in a cylindrical surface.

According to some embodiments, rays passing through the light source collimator 120 is in a fan shape (with a field angle Δβ from a direction perpendicular to an illumination plane), and the plane includes a rectangular section of the inspected objects 130 in the XOZ plane. When the inspected objects 130 move on a transport belt (for example, along Y axis), the inspected objects 130 are scanned. When the rays encounter the inspected objects 130, the rays are scattered. The scatter collimator 140 in the XOY plane operates to allow only rays scattered at a predetermined angle to be incident on the detector 150. Energy spectrum information of the scattered rays from the inspected objects are calculated by a control and processing apparatus 160 such as a computer or the like connected to the distributed light source 110 and the detector 150 based on a signal output by the detector 150.

According to some embodiments, the scatter collimator 140 is comprised of two parts. The first part includes multiple (two or three) coaxial cylindrical surfaces made of an X-ray absorbing material. In the cylindrical surfaces, circular slots are arranged at predetermined range intervals, to allow rays in a conical surface at a certain angle to pass through. The second part includes a layer made of an X-ray absorbing material in the XOY plane, which has a linear slot arranged on a certain segment of the Y axis. The combination of the two parts determines an angle at which rays are incident on the detector, and a width of the slots and a range interval between the slots are decided according to the requirements for an angle resolution and a spatial resolution of the system.

Figure 2:
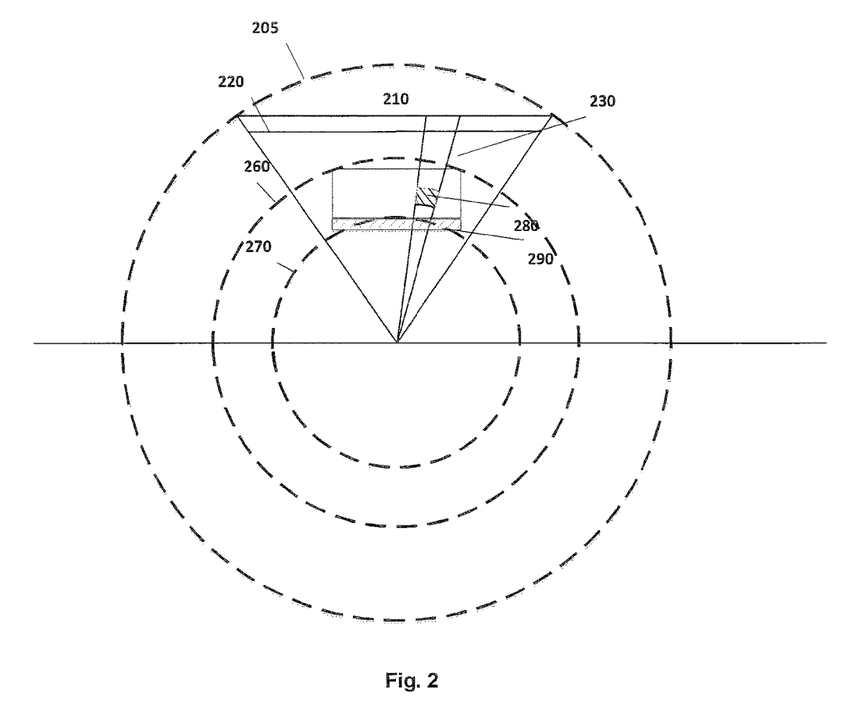
FIG. 2 is a diagram of a light source distribution and a detection region in an inspection device according to another embodiment of the present disclosure.

FIG. 2 is a diagram of a light source distribution and a detection region in an inspection device according to another embodiment of the present disclosure. The inspection device according to the present embodiment uses a distributed light source 210 to obtain an inverted fan-shaped beam which is converged to an origin under the control of a light source collimator 220. In some embodiments, there are multiple light source distributions. In the first light source distribution, the light source points are distributed over an arc 205 with a radius of R and with the origin as a center, and the light source collimator is distributed in a radial direction in front of the light source points. In the second light source distribution, the light sources are distributed over a linear segment, shown as a bold black line illustrated in FIG. 2. The light source points 210 are distributed over a linear segment, and the light source collimator 220 is arranged on a beam output path of the source points. The collimated ray beam is converged along the radial direction of the fan, is transmitted through inspected objects 230 between an inspection region outer circle 260 and an inspection region inner circle 270, and is scattered (diffracted). The control and processing apparatus 160 controls particular source points in the distributed ray source 210 to generate rays according to input position information of a region of interest in the inspected objects, so as to inspect the region of interest. For example, as shown in FIG. 2, particular source points in the distributed light source 210 are controlled to emit a beam, so that particular portions (Region Of Interest (ROI)) of the inspected objects 130 may be inspected. The detection region is a part of a ring region enclosed by an arc of the detection region outer circle 260, an arc of the detection region inner circle 270, and rays emitted from two ends of the light source to the origin, as shown in FIG. 2. The inspected objects 280 may be inscribed with the ring region, and move along the transport belt 290 in a direction perpendicular to the paper plane. It is assumed that the inspected objects are in a cubic shape, and have a width of l and a height of h in FIG. 2. In this case, a field angle of the light source with respect to the origin is:

$$\alpha = 2\arctan\frac{l}{2R_1}.$$

A length of the arc-shaped light source distribution is:

$$\overline{s\_S} = 2R\arctan\frac{l}{2R_1},$$

A length of the straight line-shaped light source distribution is:

$$s\_L = 2R\sin\left(\arctan\frac{l}{2R_1}\right).$$

Wherein, R is a radius of the arc-shaped light source, and $R_1$ is a distance between a bottom surface of the objects and the origin of the coordinates.

In general, multiple light source points may be distributed within this length of segment (at certain angle intervals), and individually emit a beam under the control of a control system. Alternatively, several adjacent light source points form a group to individually emit a beam as a group. The region 280 in FIG. 2 is a ROI, and may be a suspicious material region which is marked by a CT system or a transmission inspection system in a former stage.

Figure 3:
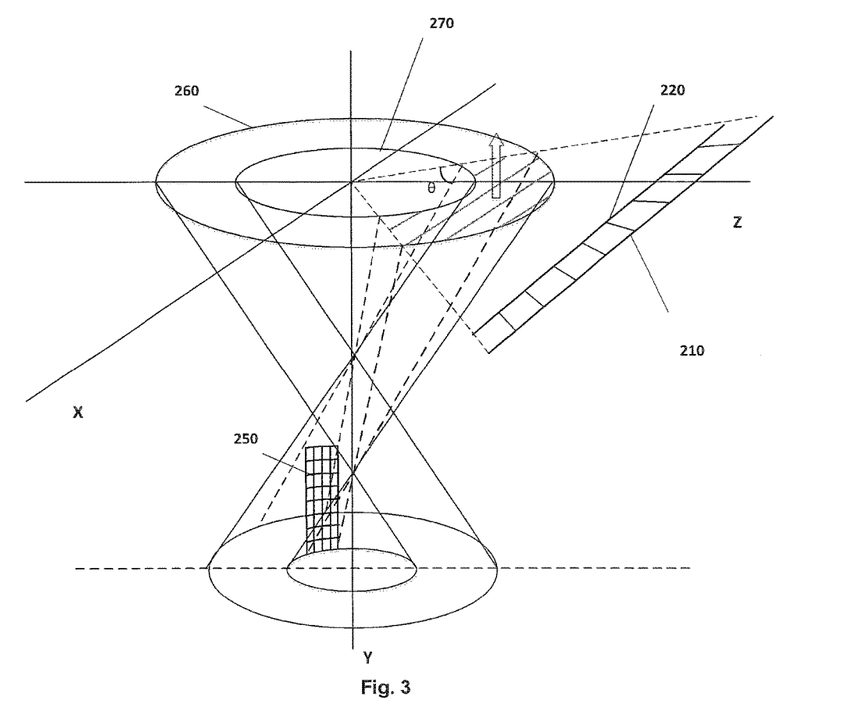
FIG. 3 is a structural diagram illustrating an inspection device detecting rays scattered at a fixed angle according to an embodiment of the present disclosure.

FIG. 3 is a structural diagram illustrating an inspection device detecting rays scattered at a fixed angle according to an embodiment of the present disclosure. As shown in FIG. 3, in an illumination plane of an inverted fan-shaped beam generated by the distributed light source 210 through the light source collimator 220, on arcs with a convergence point (an origin of the coordinates) as a center and with different radiuses, rays which are scattered at a certain angle relative to an incident ray (radius) may be converged to a point on the Y axis. These rays are distributed in a conical surface with a vertex on the Y axis and a half cone angle of $$\frac{\pi}{2} - \theta,$$

wherein θ is scattering angle. After scattered rays in conical surfaces are converged to different points on the Y axis, the scattered rays continue to diverge. In this case, the scattered rays are still distributed in a conical surface with the same vertex, the same cone angle, and opposite opening direction, as shown in FIG. 3, to form a funnel-shaped geometry. A particular scatter collimator is arranged in the XOY plane to operate on the scattered rays, so that only the scattered rays which satisfy the above described condition may be transmitted to the detector along the funnel-shaped conical surface.

As shown in FIG. 3, in the illumination plane (XOZ plane), an arc 260 with the origin as a center and with a large radius corresponds to a cone with a vertex having a large Y coordinate, and the scattered rays diverge through the convergence vertex and are projected to an arc on the bottom of the detector 250. In the illumination plane, an arc 270 with the origin as a center and with a small radius corresponds to a cone with a vertex closer to the origin of the coordinate system, and the scattered rays diverge through the convergence point and are projected to an arc on the top of the detector 250. Thus, scattered rays from different positions in the illumination plane are projected to different detection units of the cylindrical detector 250. In cooperation with uniform motion of the objects along the Y axis, the inspection device has a three-dimensional positioning capability for the inspected objects, and may measure multiple ROIs in the detection region at the same time.

An area of the detector according to the embodiments of the present disclosure is much smaller than that in a case of parallel beams in the related art, which reduces the required amount of detectors. This is because the rays have a certain convergence performance, and therefore the size of the detector may be adjusted according to the requirements for the spatial resolution of the system.

The advantage of the inspection device according to the embodiments of the present disclosure is that the convergence feature of the inverted fan-shaped light is utilized, and a funnel-shaped detection structure is skillfully adopted. This structure may control the required size of the detector according to the requirements for the spatial resolution of the system. In the design of a system having a three-dimensional positioning capability, the device according to the present embodiment may provide a high efficient and high insensitive data collection measure while reducing the required area of the detector.

In some embodiments, the scattered rays are distributed in a series of coaxial conical surfaces. In some embodiments, the scatter collimator may be designed as a series of parallel coaxial conical surfaces made of an X-ray absorbing material. Thus, an angle of the scattered light may be well defined, so that the scattered light at a required particular angle may be more accurately received. However, there are higher requirements on the collimator.

In other embodiments, some parallel slices may be used to operate on the scattered light. However, as the scattered light is actually distributed in conical surfaces with a certain radian, the parallel plate collimators with slots may bring a certain offset in the angle.

Figure 4:
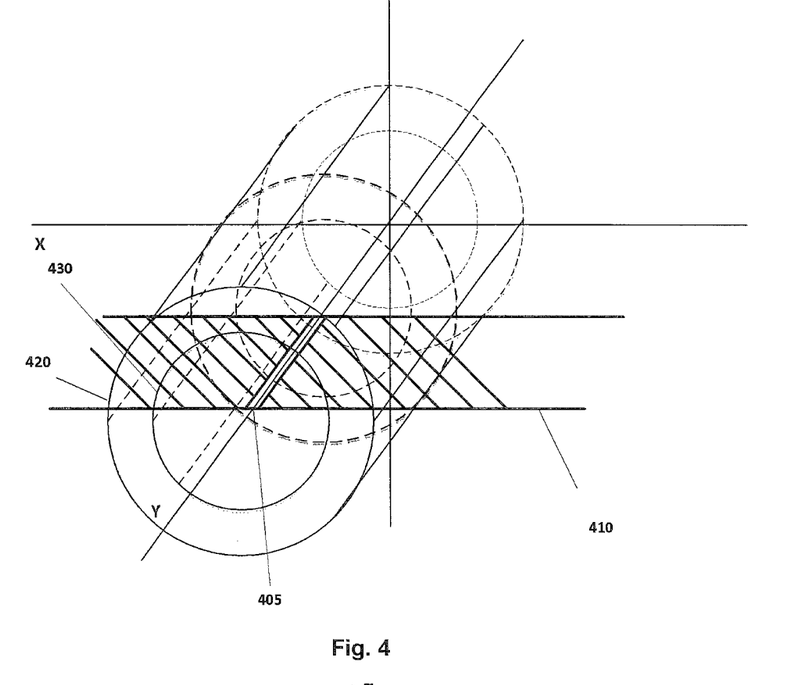
FIG. 4 illustrates a structural diagram of a scatter collimator according to an embodiment of the present disclosure.

In the embodiment illustrated in FIG. 4, another construction of a scatter collimator is illustrated. As shown in FIG. 4, the scatter collimator is comprised of two parts. The first part is two coaxial embedded semi-cylindrical surfaces 420 and 430 with an axis of Y axis (for example, the semi-cylindrical surfaces are only above the XOY plane), and the second part is a plate arranged in the XOY plane, which is related to the funnel-shaped geometrical model used in the design. As when the X-rays are transmitted through objects, some rays scattered at an angle θ are converged to the Y axis along different conical surfaces, and are intersected with the cylindrical collimator to form many arcs distributed on the cylindrical surfaces. According to the geometry and the requirements for an angle resolution of the system, a series of slots are arranged in corresponding positions of two cylindrical surfaces, so that scattered rays which are incident on the conical surfaces at a certain angle may be transmitted through the slots. A plate collimator 410 arranged in the XOY plane below the cylindrical collimator has a linear slot 405 arranged on the Y axis, which enables scattered rays which are converged on the Y axis to be transmitted and illuminated on corresponding parts of the detector. With the design of the scatter collimator illustrated in FIG. 4, it may be ensured that rays scattered at a fixed angle may be detected by the detector in accordance with a funnel-shaped geometry illustrated in FIG. 3. In some embodiments, a detector (such as a CdZnTe (CZT) detector or a High-Purity Ge (HPGe) detector) having an energy resolution capability measures X-rays scattered at a fixed angle from different ROIs, and may obtain a coherent scattering image (or diffraction pattern) of corresponding materials in terms of energy distribution. Lattice constant information of the materials may be obtained by analyzing peak positions of the spectrum. In a processing apparatus, the categories of the materials may be recognized by comparing the lattice constant information with reference spectral lines of various materials (such as explosives) in a database.

Figure 5:
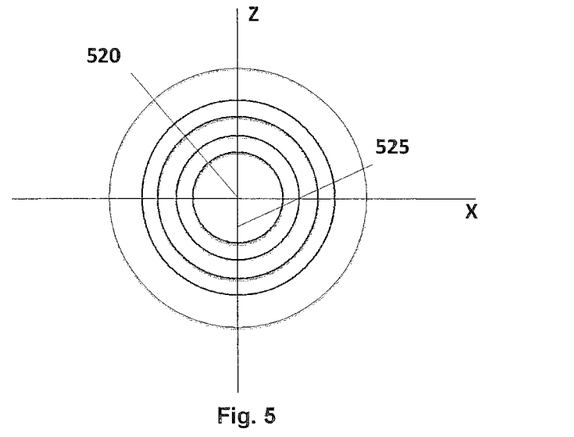
FIG. 5 illustrates a structural diagram of a scatter collimator according to another embodiment of the present disclosure.

FIG. 5 is a structural diagram of a scatter collimator according to another embodiment of the present disclosure. As shown in FIG. 5, the scatter collimator is comprised of two parts. A structure above the XOY plane comprises embedded spherical surfaces (with a center on the Y axis which is perpendicular to the paper plane). Vertexes of conical surfaces on which the rays scattered at a fixed angle are distributed are located on the same diameter (Y axis) of a virtual sphere. Thus, intersection lines between the conical surfaces and the spheres are arcs on the spheres. With the embedded structure, multiple slots 525 define accurate incident direction of the scattered rays. A plate collimator arranged in the XOY plane below the spherical collimator 520 has a linear slot on the Y axis. This further operates to enable only the scattered rays which are converged on the Y axis to be transmitted and illuminated on the corresponding parts of the detector.

The scatter collimator according to the embodiments of the present disclosure is comprised of two parts, which commonly operate to enable only the scattered rays which are distributed in conical surfaces with particular vertexes to be incident on the detector. With the funnel-shaped geometry, the detector is arranged in a position below the convergence point of the light, i.e., a lower part of the funnel (as shown in FIG. 3). In theory, a more accurate design of the scatter collimator may be used to reduce the angle error of the system. If the scatter collimator is arranged before the convergence point of the light, the collimator with slots cannot be used to operate on the scattered light, and when a two-dimensional detector is used, "crosstalk" in the X-axis direction may occur, which results in a large error.

Figure 6:
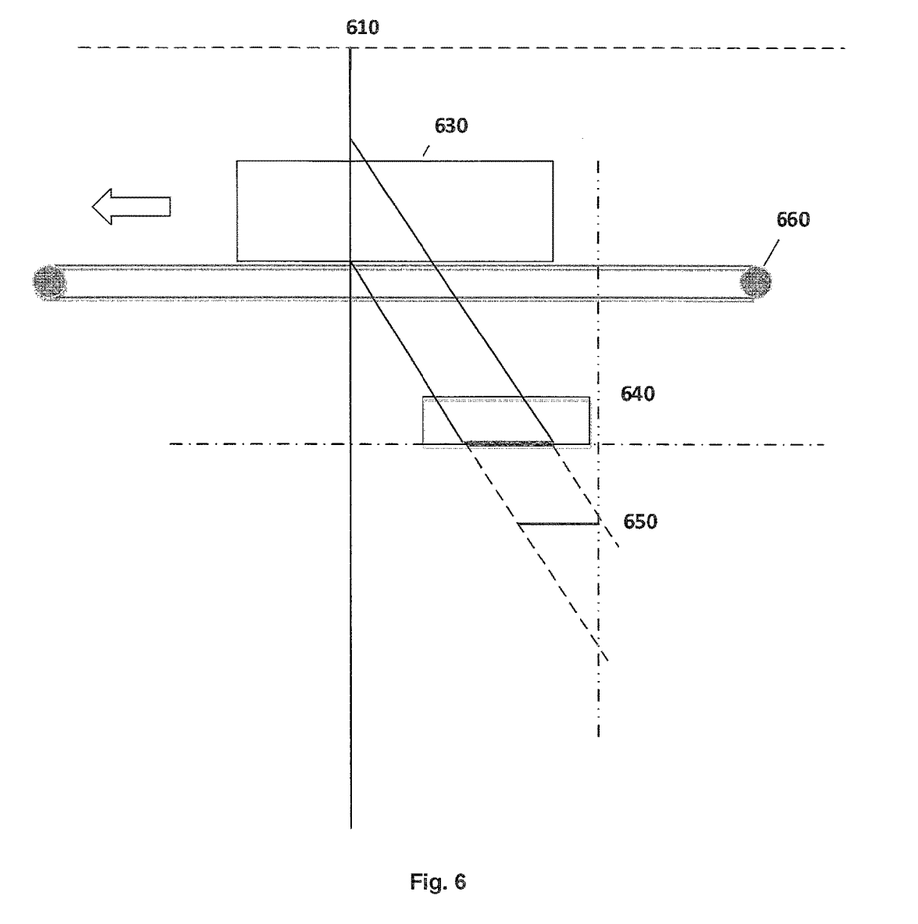
FIG. 6 illustrates a side view of an inspection device according to an embodiment of the present disclosure.

FIG. 6 illustrates a side view of an inspection device according to an embodiment of the present disclosure. The device according to the embodiments of the present disclosure is based on the coherent X-ray scattering technology, and is used as a detection apparatus for detecting explosives in a next stage, and may be connected in series with a CT detection system in a former stage. The detection apparatus in the latter stage obtains position information of the suspicious materials in the inspected objects 630 from the CT detection apparatus. FIG. 6 illustrates relative positions of various parts of the whole system. A ray machine 610 is arranged on the top of the system in a direction perpendicular to the paper plane, and the inspected objects 630 move at a constant speed horizontally to the right when the inspected objects 630 are driven by a transport belt 660. The scattered rays are projected to the detector 650 via a scatter collimator 640 below the transport belt. In the whole process, beam emission of the distributed ray machine and information recording and processing of the detector for corresponding parts are controlled by a Personal Computer (PC) or another processing system. The detectors 650 and the ray machine 610 need not to move mechanically, and the transport belt 660 needs not to be stopped, which improve the efficiency of detection of the whole system.

Figure 7:
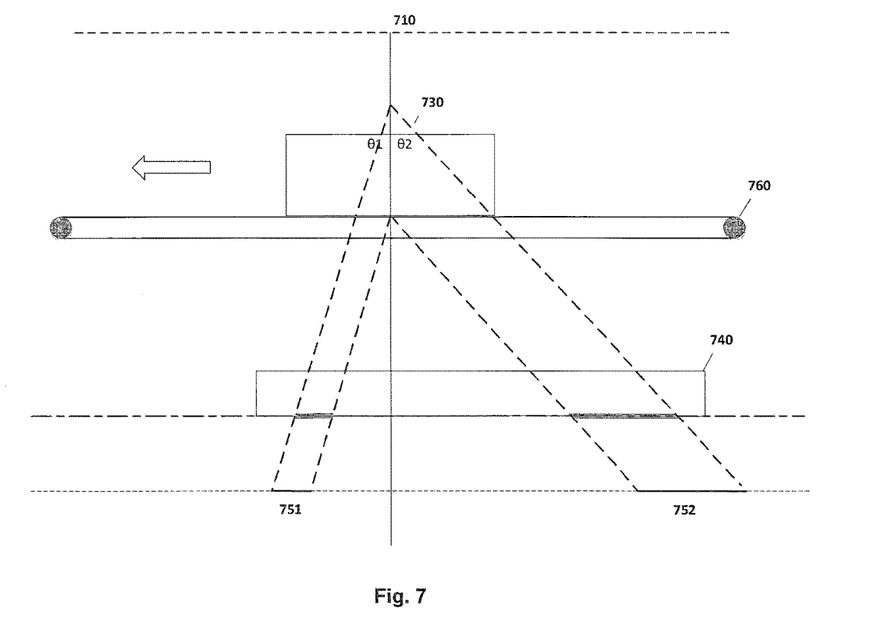
FIG. 7 illustrates a side view of an inspection device according to another embodiment of the present disclosure.

FIG. 7 illustrates a side view of an inspection device according to another embodiment of the present disclosure. The structure in FIG. 7 differs from the structure in FIG. 6 in that the system has a scatter collimator 740 and has a detector 751 and a detector 752 respectively for different scattering angles on two sides of the illumination plane. A ray machine 710 is arranged on the top of the system in a direction perpendicular to the paper plane, and the inspected objects 730 move at a constant speed horizontally to the right when the inspected objects 730 are driven by a transport belt 760. The scattered rays are projected to the detectors 751 and 752 via the scatter collimator 740 below the transport belt. Thus, information of rays scattered at two fixed angles may be measured at the same time. The consideration of this design is that according to the equation (1), the energy E of the X-rays is generally distributed in a range of 20~100 keV, and a lattice constant is on the order of $10^{-10}$ m, and thus, a typical scattering angle is small, and the above equation may be approximated as:

$$E\theta \approx \frac{hc}{d} \quad (2)$$

wherein n is equal to 1. According to the equation (2), it can be seen that when coherent scattering measurement is implemented on particular objects, if an angle θ increases, a corresponding peak position of the obtained energy spectrum shifts to the left (i.e., decreases), that is, the energy of the X-ray corresponding to the characteristic peak decreases; and when θ decreases, the peak of the spectrum shifts to the right. For a detector, the energy resolution is high for a high energy part, but a small angle θ corresponds to the high energy part at this time, and therefore, a corresponding angle resolution $$\frac{\Delta\theta}{\theta}$$

of the system degrades. According to the designs and experiments of systems, coherent X-ray scattering system is more sensitive to the angle resolution. Therefore, when measurement is implemented at a small angle, the whole resolution will degrade, and the quality of the obtained spectral lines will also decrease. However, there is a case needed to be considered, i.e., in luggage, when there is a strong X-ray absorbing material in the path of scattered light, or the objects are thick, a low energy part of the polychromatic X-ray will be strongly absorbed, and ray hardening may influence the spectral lines. In this case, when measurement is implemented at a large angle θ, the hardening may result in serious influences. Thus, in different luggage cases, the results given at different angles may be different, and there is a relatively suitable angle. Therefore, a structure for implementing measurement at two angles at the same time is designed as shown in FIG. 7, wherein $\theta_1 < \theta_2$ (for example, $\theta_1 \approx 3°$, and $\theta_2 \approx 5°$). As a result, it may be judged which angle is relatively suitable for measurement according to the density of the material and position information obtained by the CT system in the former stage or spectral lines for two angles are jointed, which may improve the signal to noise ratio, enhance the accuracy of judgment, and reduce the error rate.

Figure 8:
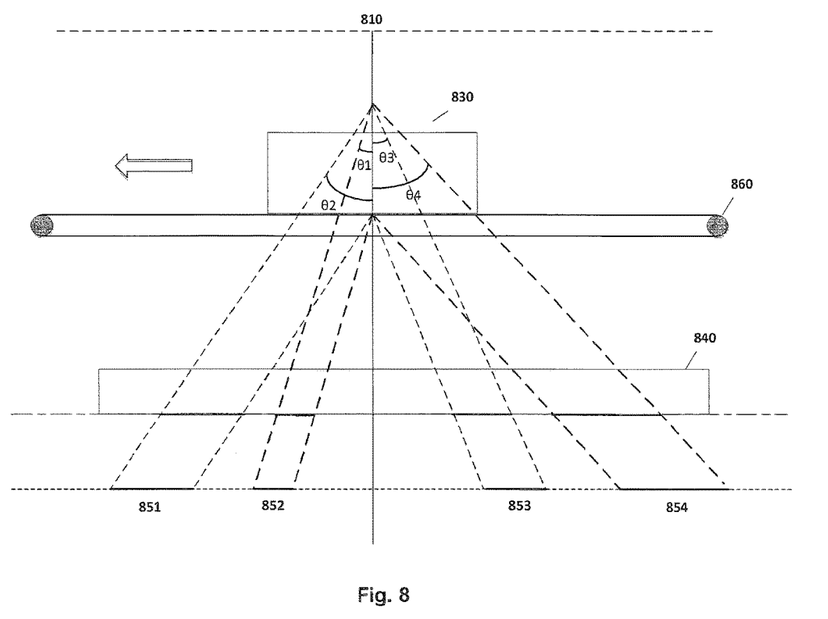
FIG. 8 illustrates a side view of an inspection device according to a further embodiment of the present disclosure.

FIG. 8 illustrates a side view of an inspection device according to a further embodiment of the present disclosure. In this mode, a system is allowed to measure energy spectrum curves of X scattered rays at four angles at the same time, to obtain four spectrograms. These four spectrograms may be jointed (to obtain angle-energy joint distributions at four angles) so as to improve the signal to noise ratio of the data to be processed. The structure in FIG. 8 differs from the structure in FIG. 6 in that the system has a scatter collimator 840, and has a group of detectors 851 and 852 and a group of detectors 853 and 854 respectively for different scattering angles on two sides of the illumination plane. A ray machine 810 is arranged on the top of the system in a direction perpendicular to the paper plane, and the inspected objects 830 move at a constant speed horizontally to the right when the inspected objects 830 are driven by a transport belt 860. The scattered rays are projected to the detectors 851 and 852 and the detectors 853 and 854 via the scatter collimator 840 below the transport belt. In this way, information of rays scattered at two fixed angles may be measured at the same time. As shown in FIG. 8, illumination ranges of two groups of scattered rays on the collimator are separated on either side of the illumination plane, to avoid interference to each other. Rays at two angles are illuminated on two cylindrical detectors. After four energy spectrum curves are obtained, an energy spectrum curve with the best effects may firstly be selected for judgment, or the four curves for different angles may be jointed to improve the signal to noise ratio of the curves.

Figure 9:
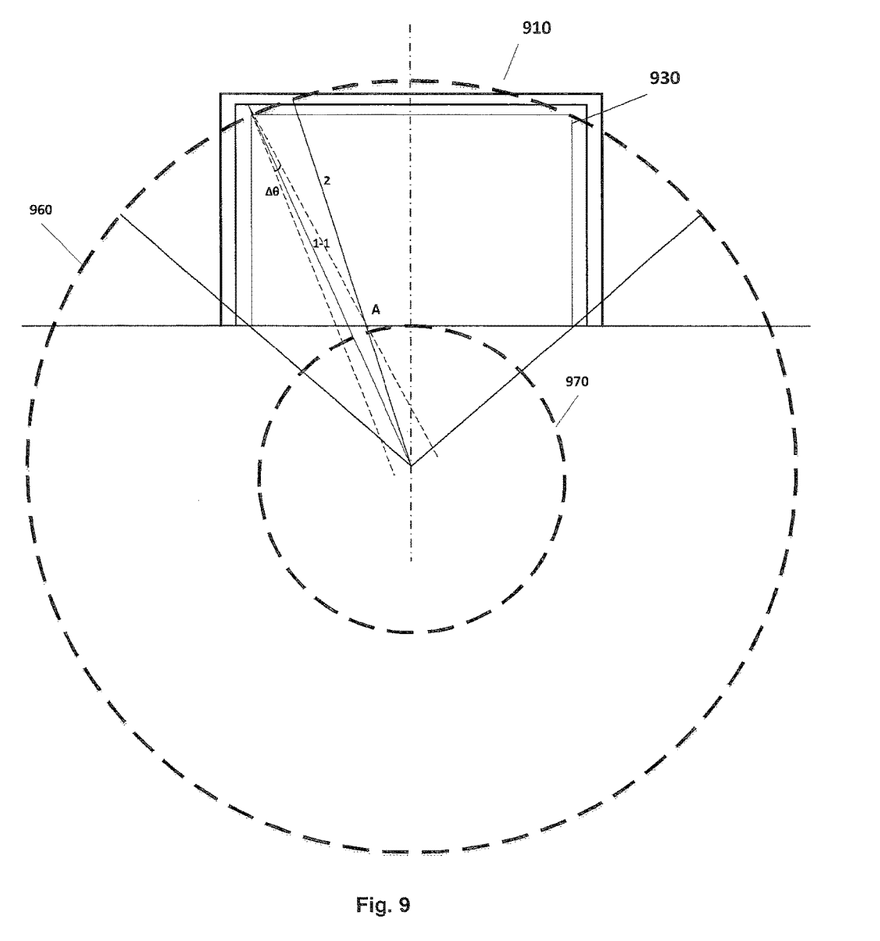
FIG. 9 illustrates a structural diagram of a light source in an inspection device according to an embodiment of the present disclosure.
Figure 10:
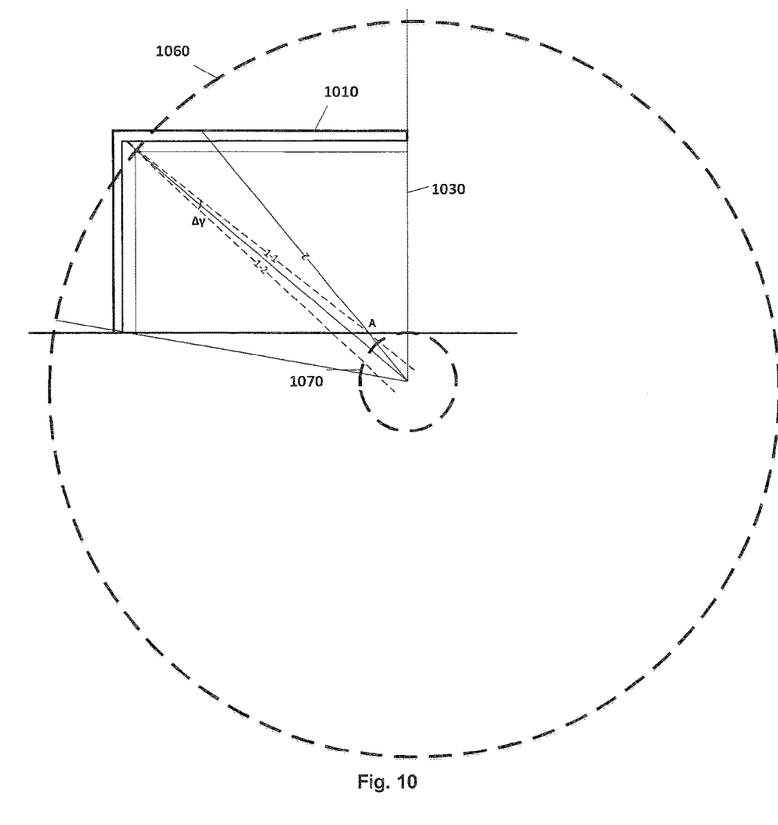
FIG. 10 illustrates a structural diagram of a light source in an inspection device according to another embodiment of the present disclosure.

FIGS. 9 and 10 illustrate more effective structural diagrams, and the primary purpose is to reduce the size of the whole system device. That is, the defect that the size of the whole system is large due to a large light source distribution range in an arc or a linear segment is improved.

FIG. 9 illustrates a U-shaped (or inverted U-shaped) design. The design is characterized in that the system is symmetric from left to right, and there is no difference in illuminated rays for the detected cubic objects (with a rectangular section). In the mode illustrated in FIG. 9, an inverted U-shaped distributed light source 910 and a light source collimator 930 are arranged in a detection region between a distributed light source simulation circular orbit radius/detection region outer circle radius 960 and a detection region inner circle radius 970. The U-shaped design enables decrease in a size of the distributed light source in a direction perpendicular to a transportation direction of the transport belt, and the light source nearly adjoins the rectangular detection region. In addition, this design makes significant decrease in the detection region inner circle radius become possible, and at the same time, reduces the height of the whole system.

In the embodiment, as the light source is in a distributed mode, light source points are arranged at certain angle intervals. Therefore, there is a problem about the sampling interval. In order to maintain the angle resolution, a field angle $\Delta\gamma$ of a ray emitted by each light source point should be small enough, as shown in FIG. 9. An analysis on a change in the angle resolution due to the field angle of each ray will be described below. Assuming that after each ray passes through the light source collimator, each ray has a field angle of $\Delta\gamma\approx0.4°$, an edge ray 1-1 of ray 1 intersects with ray 2 at a point A, and these rays may be scattered from the objects at point A and transmitted to a detector along the same trajectory. In this case, the corresponding scattering angles are different. When the scatter collimator defines a scattering angle of 3°, an error in the angle due to $\Delta\gamma$ is about $$\frac{\Delta\theta}{\theta} < 5.72\%$$

without considering an error in the angle due to the actual scatter collimator. Assuming that the scatter collimator may accurately define the incident angle for the detector, if the angle defined by the scatter collimator is changed to 2.91°, due to the error resulting from $\Delta\gamma$, the possible scattering angle range of the scattered rays incident on the detector is 2.91°~3.09°, and an average angle is still 3°, with a maximal error of $$\frac{\Delta\theta}{\theta} < 3.00\%.$$

However, in a case that the angle resolution is ensured, the rays cannot cover the whole section of the objects. In order to avoid or reduce the missing rate due to measurement in a non-complete-cover manner, it needs to ensure that an interval between two rays is small enough. This interval needs to be set according to a size range of objects to be actually inspected. In the present embodiment, it is proposed that an interval between two adjacent rays is no more than 12 mm on an arc of the detection region outer circle. In a case of FIG. 9 and the above parameters, if light source points are arranged at 0.6° intervals, a total of 227 light source points are needed. Then, a maximal interval between the rays is $\Delta x=10.79$ mm. As the rays are convergent, and the actual detection region is rectangular and is inside the arc of the outer circle, in the detection region, this standard may be satisfied.

Figure 11:
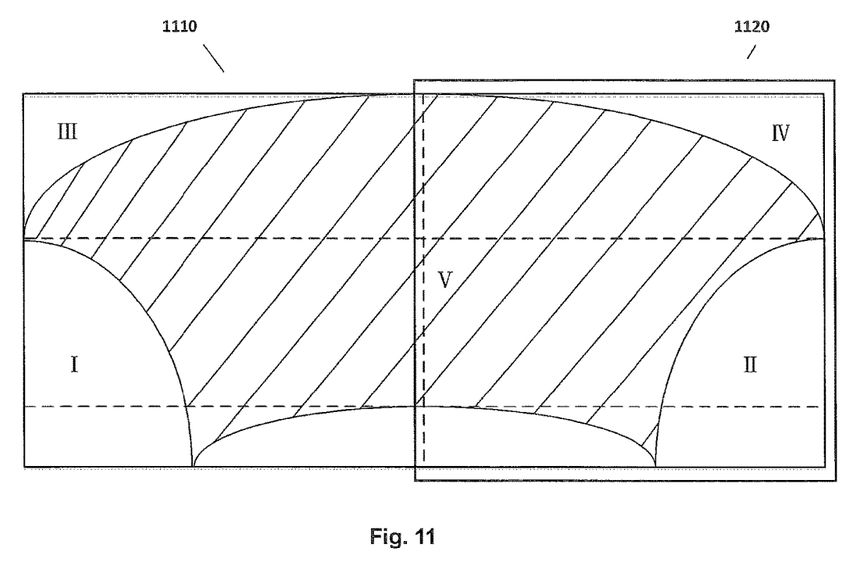
FIG. 11 illustrates a distribution region of scattering information of a rectangular section (actual detection region) of objects on a cylindrical detector.

In addition, as shown in FIG. 3, the detector records information of a part of ring region in the detection plane, but the actual monitored region is merely a rectangle inscribed with the ring region. Therefore, on the cylindrical detector as described above, there are some regions without useful information, for example, regions I, II, III, IV or the like as illustrated in FIG. 11, and a useful region is merely a part of the rectangular region which is projected through the funnel-shaped conical surface on the cylindrical detector, for example, region V illustrated in FIG. 11 (in a symmetric structure condition).

FIG. 10 illustrates an L-shaped design mode. The design of the system is non-symmetrical, but the basic principle and the measurement manner are the same. In the mode illustrated in FIG. 10, an inverted L-shaped distributed light source 1010 and a light source collimator 1030 are arranged in a detection region between a distributed light source simulation circular orbit radius/detection region outer circle radius 1060 and a detection region inner circle radius 1070. In the present embodiment, a detector is arranged in a non-symmetric form in a position which is below and to the right of the objects. The distribution of the scattered rays from the rectangular region on the detector is shown as a region 1120 illustrated in a block of FIG. 11 (an L-shaped structure).

Compared with the design in FIG. 9, in the design in FIG. 10, the required size of the detector is comparable, i.e., the size of the design in FIG. 9 and the size of the design in FIG. 10 are much smaller than that in a parallel beam mode. Due to the use of the distributed light source, a maximal interval between the sampling points (a maximal interval between rays) may be smaller than 12 mm. Due to the increase in $R_2$, an error in the angle due to $\Delta\gamma$ increases. Assuming that $\Delta\gamma=0.4°$, a scattering angle defined by the scatter collimator is 2.85°, and an average scattering angle of the scattered rays is 3°, the error in the angle is about $$\frac{\Delta\theta}{\theta} < 5.11\%,$$

which is slightly poorer than that in the U-shaped design. Therefore, there are higher requirements for the light source collimator, and there may be a need to reduce $\Delta\gamma$. However, $\Delta\gamma$ is not suitable to be too small; otherwise, the counting rate may be significantly reduced. In terms of the shape, there is one less arm in the L shape than in the U shape, and therefore, the non-symmetrical design in FIG. 9 needs a reduced number of light source points. No matter whether to use the U-shape distribution or the L-shape distribution, the designs in the two modes may reduce the size of the whole system.

The embodiments of the present disclosure propose to use a two-dimensional cylindrical detector, so that the system may measure information of various points in a section plane of materials at the same time and optimize the three-dimensional positioning capability. Multiple light sources may illuminate at the same time, so as to significantly enhance the intensity of rays in the detection plane. In this way, the system may have a better signal-to-noise ratio, and further improve the efficiency of detection. Compared with the method using parallel beams, the required size of the detector in the embodiments of the present disclosure is smaller. Meanwhile, in another system structure of the design, energy distribution curves of rays scattered at two different angles may also be measured at the same time. Therefore, the system may be used according to practical conditions or by jointing the information obtained for two angles to improve the material resolution capability of the system.

Other embodiments of the present disclosure disclose a coherent X-ray scattering system using a distributed light source for an inverted fan-shaped beam, which uses a detector having an energy resolution capability to measure an energy distribution of X-rays scattered at a fixed angle to obtain a lattice constant of the materials, thereby recognizing the categories of the materials.

The distributed light source is distributed in an arc or a straight line. The rays pass through the objects along a radial direction and are converged to the origin of the coordinate system under the control of the light source collimator. Position information of suspicious materials from the CT in a former stage is received by a light source processing system, which specifically controls several light source points in corresponding positions to emit beams with purpose, to illuminate corresponding parts for targeted detection.

The detector has a cylindrical structure, and is used in cooperation with the collimator which is designed accurately. Scattered rays from different positions in the detection plane are illuminated on different positions of the detector, and position information of suspicious materials from the CT in the former stage is received by a data acquisition system, which specifically acquires signals of detection units in some positions.

The collimator of the whole system is divided into two parts, i.e., a light source collimator and a scatter collimator (or referred to as detector collimator). The purpose of the light source collimator is to define directions of rays emitted from light source points in different positions, so that the rays passing through the collimator are in an inverted fan-shaped beam mode, and are transmitted through the detection region and converged to the origin of the coordinate system. The scatter collimator controls the angles of the scattered rays which are incident on the surface of the detector, to only allow rays which are scattered at a fixed angle θ and in a certain conical surface to pass and be recorded by the detector.

In the whole detection process, the objects are continuously transported through the detection region when the objects are driven by the transport belt. The X light source and the detector need not to be moved. After the energy spectrum curves of the scattered rays of the suspicious materials are obtained, the lattice constant $d_i$ may be calculated according to the peak positions $E_i$ and other fixed parameters, and the curves are compared with spectral lines of various materials in the system data, so as to recognize and finally determine the categories of the materials, and thus decide whether the materials are explosives.

In some embodiments, in combination with the inverted fan-shaped beam design solution and the distributed light source design, rays emitted by the light source have a convergence trend, which may largely reduce the area of the detector as compared with the parallel beam mode. In some embodiments, the size of the detector in the inspection device is merely about 15% of the required area of the detector in the parallel beam mode, which reduces the system cost.

In addition, in some embodiments, a detector collimator and a two-dimensional detector which are particularly designed are used, so that the detector and the light source need not to be moved in the process of detecting the luggage in the present disclosure, which reduces the mechanical complexity of the system, and increases the speed, stability, and accuracy of the inspection in the system. Meanwhile, the inspection method according to the present disclosure may be used to measure multiple ROIs at the same time, and individually measure an object in any position of a luggage. Compared with the inverted fan-shaped mode in the related art, multiple light sources may emit rays at the same time, to significantly enhance intensity of rays in the detection plane. In this way, the system has better signal-to-noise ratio and efficiency of detection.

In other embodiments, a U-shaped or L-shaped light source distribution manner is used to reduce the size of the whole system.

Therefore, the above description and embodiments of the present disclosure are merely used to describe the inspection device, inspection method, and inspection system according to the embodiments of the present disclosure by means of illustrative examples, and are not intended to limit the scope of the present disclosure. Variations and amendments made to the embodiments of the present disclosure are possible. Other feasible alternative embodiments and equivalent variations of elements in the embodiments are obvious to an ordinary skilled in the art. Other variations and amendments made to the embodiments of the present disclosure do not go beyond the spirit and protection scope of the present disclosure.

We claim:

1. An inspection device, comprising:
    a distributed ray source comprising multiple source points, wherein the various source points can emit beams individually or several adjacent light source points form a group to individually emit a beam as a group;
    a light source collimator arranged at a ray beam output end of the distributed ray source, and configured to converge the rays generated by the distributed ray source into a convergence point along fan-shaped radial lines to form an inverted fan-shaped ray beam;
    a scatter collimator configured to only allow rays scattered at one or more particular scattering angles which are generated by the rays from the light source collimator interacting with inspected objects to pass;
    at least one detector arranged on the downstream of the convergence point and the scatter collimator, each detector comprising multiple detection units which have an energy resolution capability and are substantially arranged in a cylindrical surface to receive the scattered rays passing through the scatter collimator; and
    a processing apparatus configured to calculate energy spectrum information of the scattered rays from the inspected objects based on a signal output by the detectors.

2. The inspection device according to claim 1, wherein the processing apparatus is further configured to calculate a lattice constant based on peak position information included in the energy spectrum information of the scattered rays, and judge whether the inspected objects include explosives or dangerous objects by comparing the calculated lattice constant with a predetermined value.

3. The inspection device according to claim 1, further comprising a control apparatus configured to control a particular source point in the distributed ray source to generate a ray according to input position information of an region of interest in the inspected objects to inspect the region of interest.

4. The inspection device according to claim 1, wherein the multiple source points of the distributed ray source are distributed in an arc shape, a straight line shape, a U shape, an inverted U shape, an L shape, or an inverted L shape.

5. The inspection device according to claim 1, wherein the scatter collimator comprises a bottom surface and multiple embedded cylindrical surfaces on the bottom surface, circular slots are arranged at predetermined range intervals in the multiple embedded cylindrical surfaces, and a slot is arranged on the bottom surface along an axial direction of the cylindrical surfaces.

6. The inspection device according to claim 1, wherein the scatter collimator comprises a bottom surface and multiple embedded spherical surfaces on the bottom surface, circular slots are arranged at predetermined range intervals in the multiple embedded spherical surfaces, and a slot is arranged on the bottom surface along a radial direction of the bottom surface.

7. The inspection device according to claim 1, wherein the scatter collimator is made of a ray absorbing material.

8. The inspection device according to claim 1, wherein the scatter collimator comprises multiple columns of parallel coaxial conical surfaces made of a ray absorbing material.

9. The inspection device according to claim 1, wherein the scatter collimator comprises multiple parallel slices.

10. The inspection device according to claim 1, wherein the detector is a CdZnTe (CZT) detector or a High-Purity Ge (HPGe) detector.

11. An inspection system, comprising:
a bearing member configured to bear inspected objects to move linearly;
a first scanning stage comprising a transmission imaging apparatus or a Computer Tomography (CT) imaging apparatus to implement transmission inspection or CT inspection on the inspected objects;
a processing apparatus configured to receive a signal generated by the first scanning stage and determine at least one region of interest in the inspected objects based on the signal;
a second scanning stage arranged a predetermined distance from the first scanning stage along a movement direction of the objects, the second scanning stage comprising:
a distributed ray source comprising multiple source points to generate rays, wherein the various source points can emit beams individually or several adjacent light source points form a group to individually emit a beam as a group;
a light source collimator arranged at a ray beam output end of the distributed ray source, and configured to converge the rays generated by the distributed ray source into a convergence point along fan-shaped radial lines to form an inverted fan-shaped ray beam;
a scatter collimator configured to only allow rays scattered at one or more particular scattering angles which are generated by the rays from the light source collimator interacting with the inspected objects to pass; and at least one detector arranged on the downstream of the convergence point, each detector comprising multiple detection units which have an energy resolution capability and are substantially arranged in a cylindrical surface to receive the scattered rays passing through the scatter collimator;
wherein the processing apparatus is configured to instruct the second scanning stage to inspect the at least one region of interest and calculate energy spectrum information of the scattered rays from the inspected objects based on the signal output by the detectors.

12. An inspection method, comprising:
generating, by a distributed ray source comprising multiple source points, wherein the various source points can emit beams individually or several adjacent light source points form a group to individually emit a beam as a group;
converging the rays generated by the distributed ray source into a convergence point along fan-shaped radial lines to form an inverted fan-shaped ray beam;
collimating, by a scatter collimator arranged on a front end of detectors, the rays to only allow rays scattered at one or more particular scattering angles which are generated by the rays interacting with inspected objects to pass;
receiving, by at least one detector, the scattered rays passing through the scatter collimator, each detector comprising multiple detection units having an energy resolution capability and is in a cylindrical surface shape, wherein the detectors are arranged on the downstream of the convergence point; and
calculating energy spectrum information of the scattered rays from the inspected objects based on a signal output by the detectors.

13. The method according to claim 12, further comprising steps of:
calculating a lattice constant based on peak position information included in the energy spectrum information of the scattered rays, and judging whether the inspected objects include explosives or dangerous objects by comparing the calculated lattice constant with a predetermined value.

14. The method according to claim 12, further comprising steps of:
controlling a particular source point in the distributed ray source to generate a ray according to input position information of an region of interest in the inspected objects to inspect the region of interest.

* * * * *